(12) United States Patent
Wei et al.

(10) Patent No.: US 10,115,915 B1
(45) Date of Patent: Oct. 30, 2018

(54) ORGANIC THIN FILM TRANSISTOR AND METHOD FOR MAKING THE SAME

(71) Applicants: Tsinghua University, Beijing (CN); HON HAI PRECISION INDUSTRY CO., LTD., New Taipei (TW)

(72) Inventors: Hao-Ming Wei, Beijing (CN); Yang Wei, Beijing (CN); Kai-Li Jiang, Beijing (CN); Shou-Shan Fan, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 0 days.

(21) Appl. No.: 15/687,619

(22) Filed: Aug. 28, 2017

(30) Foreign Application Priority Data

Apr. 28, 2017 (CN) .......................... 2017 1 0295427

(51) Int. Cl.
*H01L 51/05* (2006.01)
*H01L 51/00* (2006.01)
*C07F 7/24* (2006.01)

(52) U.S. Cl.
CPC ............ *H01L 51/0558* (2013.01); *C07F 7/24* (2013.01); *H01L 51/0048* (2013.01); *H01L 51/0059* (2013.01); *H01L 51/0077* (2013.01)

(58) Field of Classification Search
None
See application file for complete search history.

(56) References Cited

U.S. PATENT DOCUMENTS

| 5,677,546 A * | 10/1997 | Yu ....................... H01L 51/5012 |
| | | 257/103 |
| 2017/0092865 A1* | 3/2017 | Yuning ............... H01L 51/0036 |
| 2017/0352825 A1* | 12/2017 | Wei ......................... C23C 14/24 |

* cited by examiner

*Primary Examiner* — Bradley K Smith
(74) *Attorney, Agent, or Firm* — ScienBiziP, P.C.

(57) ABSTRACT

A method for forming an organic thin film transistor is provided. An interdigital electrode layer is located on a surface of the insulating substrate. An organic semiconductor layer is formed on a surface of the interdigital electrode layer. An insulating layer is located to cover the organic semiconductor layer. A gate electrode is formed on the insulating layer. A method for forming the organic semiconductor layer is provided. An evaporating source is provided, and the evaporating source and the interdigital electrode layer are spaced from each other. The carbon nanotube film structure is heated to gasify an organic semiconductor material to form the organic semiconductor layer on an interdigital electrode layer surface.

17 Claims, 15 Drawing Sheets

ORGANIC THIN FILM TRANSISTOR AND METHOD FOR MAKING THE SAME

CROSS-REFERENCE TO RELATED APPLICATIONS

This application claims priority to Chinese Patent Application No. 201710295427.2, filed on Apr. 28, 2017, the disclosure of which is incorporated herein by reference.

FIELD

The present disclosure relates to an organic thin film transistor and method for making the same.

BACKGROUND

An organic thin film transistor (OTFT) has been used in electronic papers, sensors, memories, flexible displays and integrated circuits because of having a light weight, flexibility, and a low manufacturing cost. An organic semiconductor layer can be formed on a surface of an insulating substrate by spin coating and etching. Conventionally, the organic semiconductor layer may be formed by a vapor deposition method. However, in order to form a uniform organic semiconductor layer, it is necessary to form a uniform gaseous evaporating material around a depositing substrate. Since it is difficult to control a diffusion direction of atoms of the gaseous evaporating material, most of the evaporating material can not be attached to a surface of the depositing substrate, and a deposition rate of the evaporating material is slow.

BRIEF DESCRIPTION OF THE DRAWINGS

Implementations of the present technology will now be described, by way of example only, with reference to the attached figures.

DETAILED DESCRIPTION

Figure 1:
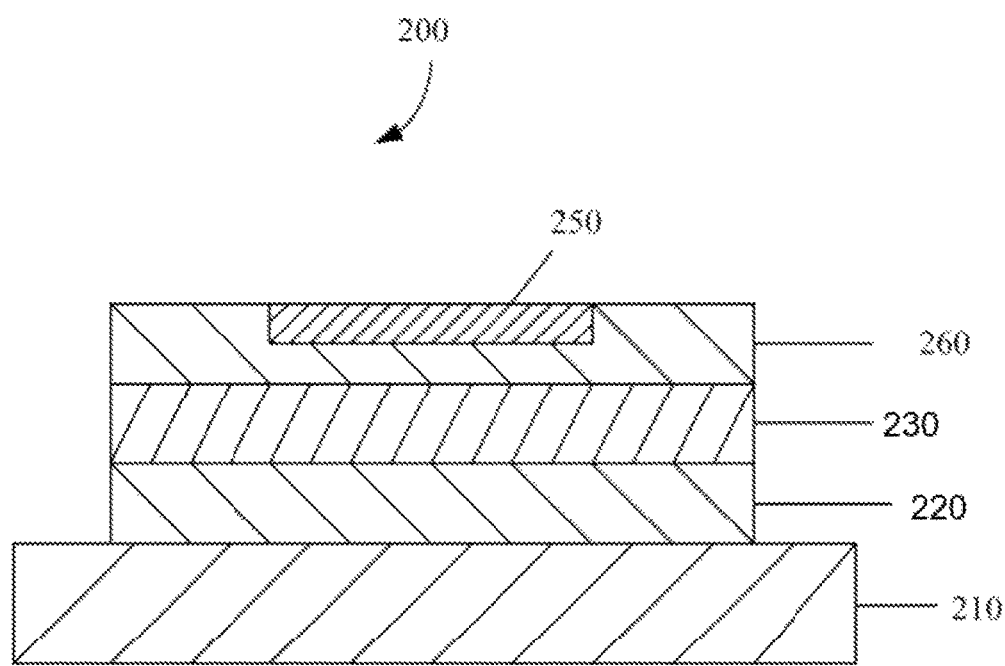
FIG. 1 is a schematic view of one embodiment of a top type organic thin film transistor.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean "at least one".

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale, and the proportions of certain parts may be exaggerated to illustrate details and features of the present disclosure better.

Several definitions that apply throughout this disclosure will now be presented.

The term "comprise" or "comprising" when utilized, means "include or including, but not necessarily limited to"; it specifically indicates open-ended inclusion or membership in the so-described combination, group, series, and the like.

Figure 2:
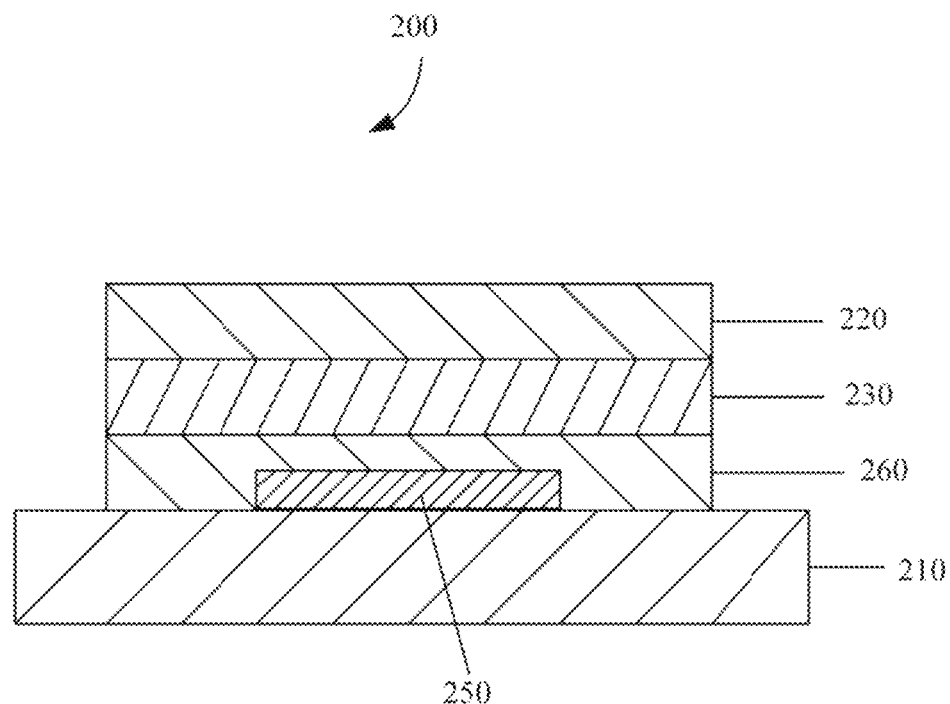
FIG. 2 is a schematic view of one embodiment of a back type organic thin film transistor.
Figure 3:
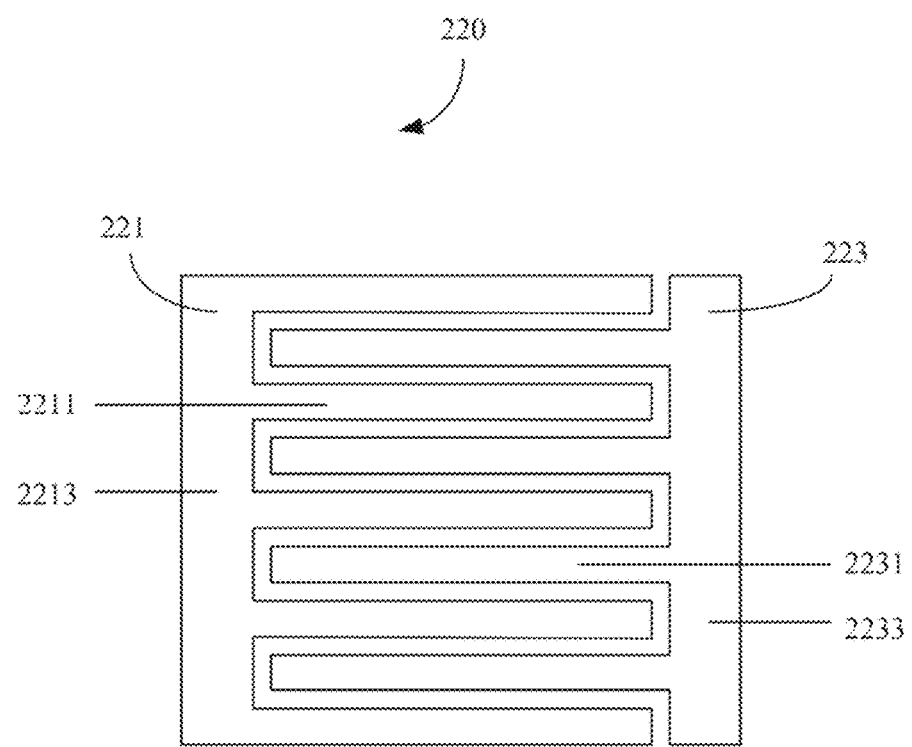
FIG. 3 is a schematic view of one embodiment of an interdigital electrode layer.

Referring to FIG. 1 to FIG. 3, in one embodiment, an organic thin film transistor 200 is provided. The organic thin film transistor 200 is located on a insulating substrate 210. The organic thin film transistor 200 comprising an interdigital electrode layer 220, an organic semiconductor layer 230, a gate electrode 250, and an insulating layer 260. The organic semiconductor layer 230 is electrically connected to the interdigital electrode layer 220. The gate electrode 250 is insulated from the organic semiconductor layer 230 and the interdigital electrode layer 220 by the insulating layer 260. The organic thin film transistor 200 may be a top gate type or a back gate type.

Referring to FIG. 1, in one embodiment, the organic thin film transistor 200 is the top gate type. The organic semiconductor layer 230 is located on a surface of the insulating substrate 210. The interdigital electrode layer 220 is located on a surface of the organic semiconductor layer 230 and is electrically connected to the organic semiconductor layer 230. The insulating layer 260 is located on the surface of the organic semiconductor layer 230. The gate electrode 250 is located on a surface of the insulating layer 260 and is insulated from the organic semiconductor layer 230 and the interdigital electrode layer 220 through the insulating layer 260.

A location of the interdigital electrode layer 220 is not limited, as long as the interdigital electrode layer 220 is electrically connected to the organic semiconductor layer 230. In one embodiment, the interdigital electrode layer 220 can located on the surface of the organic semiconductor layer 230 and is located between the insulating layer 260 and the organic semiconductor layer 230. The interdigital electrode layer 220 and the gate electrode 250 are located on a same side of the organic semiconductor layer 230 to form a coplanar organic thin film transistor. In another embodiment, the interdigital electrode layer 220 is located between the insulating substrate 210 and the organic semiconductor layer 230. The interdigital electrode layer 220 and the gate electrode 250 are located on different sides of the organic semiconductor layer 230 to form a staggered organic thin film transistor.

Referring to FIG. 2, in one embodiment, the organic thin film transistor 200 is a back gate type. The gate electrode 250 is located on the surface of the insulating substrate 210. The insulating layer 260 is located on the surface of the gate electrode 250. The organic semiconductor layer 230 is located on the surface of the insulating layer 260 and is insulated from the gate electrode 250 by the insulating layer 260. The interdigital electrode layer 220 is located on the surface of the he organic semiconductor layer 230 and electrically connected to the organic semiconductor layer 230. The organic semiconductor layer 230 is electrically insulated from the gate electrode 250 through the insulating layer 260.

The location of the interdigital electrode layer 220 is not limited, as long as the interdigital electrode layer 220 is electrically connected to the organic semiconductor layer 230. In one embodiment, the interdigital electrode layer 220 is located on the surface of the organic semiconductor layer 230, and the interdigital electrode layer 220 and the gate electrode 250 are located on different sides of the organic semiconductor layer 230 to form a reverse staggered organic thin film transistor. In another embodiment, the interdigital electrode layer 220 is located on the surface of the organic semiconductor layer 230 and located between the insulating layer 260 and the organic semiconductor layer 230. The interdigital electrode layer 220 and the gate electrode 250 are formed on a same side of the organic semiconductor layer 230 to form a reverse coplanar type organic thin film transistor.

The substrate 210 is an insulating substrate. The substrate 210 can be a hard substrate or a flexible substrate. The substrate 210 can be a glass substrate, a quartz substrate, a plastic substrate or a resin substrate.

The interdigital electrode layer 220 is a conductive layer. Referring to FIG. 3, the interdigital electrode layer 220 comprises a first interdigital electrode 221 and a second interdigital electrode 223. The first interdigital electrode 221 and the second interdigital electrode 223 are spaced from and staggered with each other. The first interdigital electrode 221 comprises a first connection part 2213 and a plurality of first interdigital parts 2211. The plurality of first interdigital parts 2211 are spaced from each other and in connection with the first connection part 2213. The first connection part 2213 is used to electrically connect with an external power source. The second interdigital electrode 223 comprises a second connection part 2233 and a plurality of second interdigital parts 2231. The plurality of second interdigital parts 2231 are spaced from each other and in connection with the second connection part 2233. The second connection part 2233 is used to electrically connect with an external power source. The plurality of first interdigital parts 2211 and the plurality of second interdigital parts 2231 are staggered and spaced from each other. A shape of the plurality of first interdigital parts 2211 and the plurality of second interdigital parts 2231 are not limited and can be selected according to actual needs. A distance between adjacent a first interdigital part 2211 and a second interdigital part 2231 is more than about 10 μm. A thickness of the interdigital electrode layer 220 is ranged from about 50 nm to 150 nm. A material of the first interdigital electrode 221 and the second interdigital electrode 223 can be a metal, an ITO, an FTO or a carbon nanotube. In one embodiment, the interdigital electrode layer 220 is a 500×500 μm² square. The material of the first interdigital electrode 221 and the second interdigital electrode 223 is a copper. The distance between adjacent the first interdigital part 2211 and the second interdigital part 2231 is about 20 μm. The thickness of the interdigital electrode layer 220 is about 50 nm.

The first interdigital electrode 221 and the second interdigital electrode 223 can be respectively used as a source electrode and a drain electrode of the organic thin film transistor 200.

The material of the organic semiconductor layer 230 may be tetracene, pentacene, hexacene, rubrene, anthracene, α-Sexithiophene(α-6T), poly-3-hexylthiophene(P3HT), polypyrrole, poly thiophene, polyphenol, poly 2,5 thiophene acetylene, copper phthalocyanine, nickel phthalocyanine, zinc phthalocyanine, free phthalocyanine, fluorinated phthalocyanine copper, fluorinated phthalocyanine chromium, fluorinated phthalocyanine zinc, free fluorinated phthalocyanine or polybenzimidazole benzophenanthroline(BBL). A organic semiconductor material 114 of the organic semiconductor layer 230 are not limited to the above materials, as long as a gasification temperature of the organic semiconductor material 114 is lower than a gasification temperature of carbon nanotubes under the same conditions, and the organic semiconductor material 114 does not react with carbon during the vapor deposition process. In one embodiment, the gasification temperature of the organic semiconductor material 114 is lower than or equal to 300° C. In another embodiment, the organic semiconductor material 114 is $CH_3NH_3PbI_3$.

Figure 4:
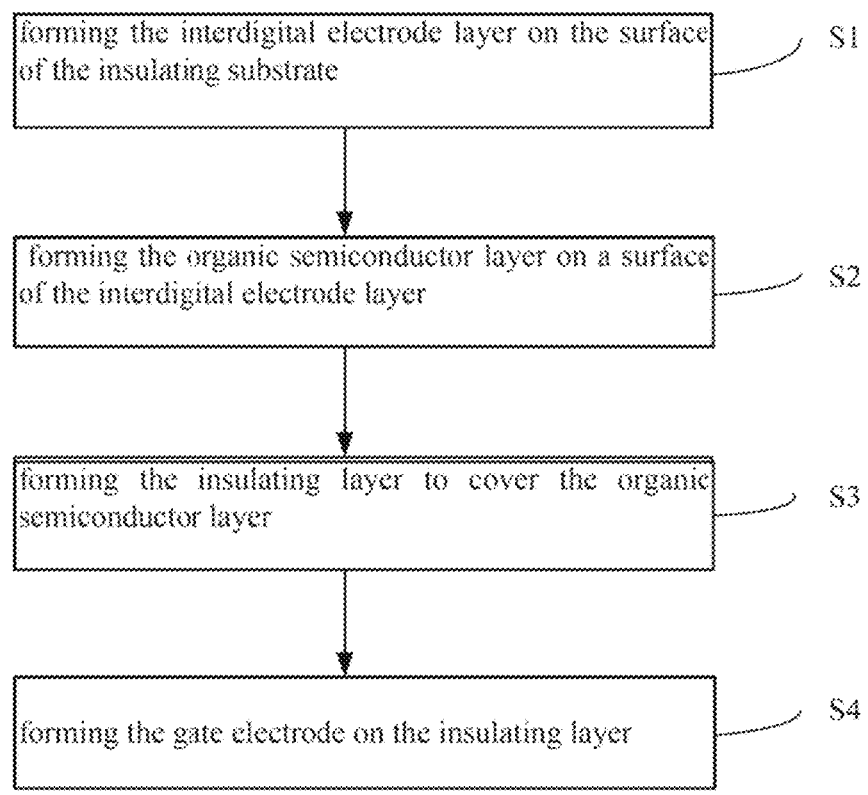
FIG. 4 is a flowchart of one embodiment of a method for forming an organic thin film transistor.
Figure 5:
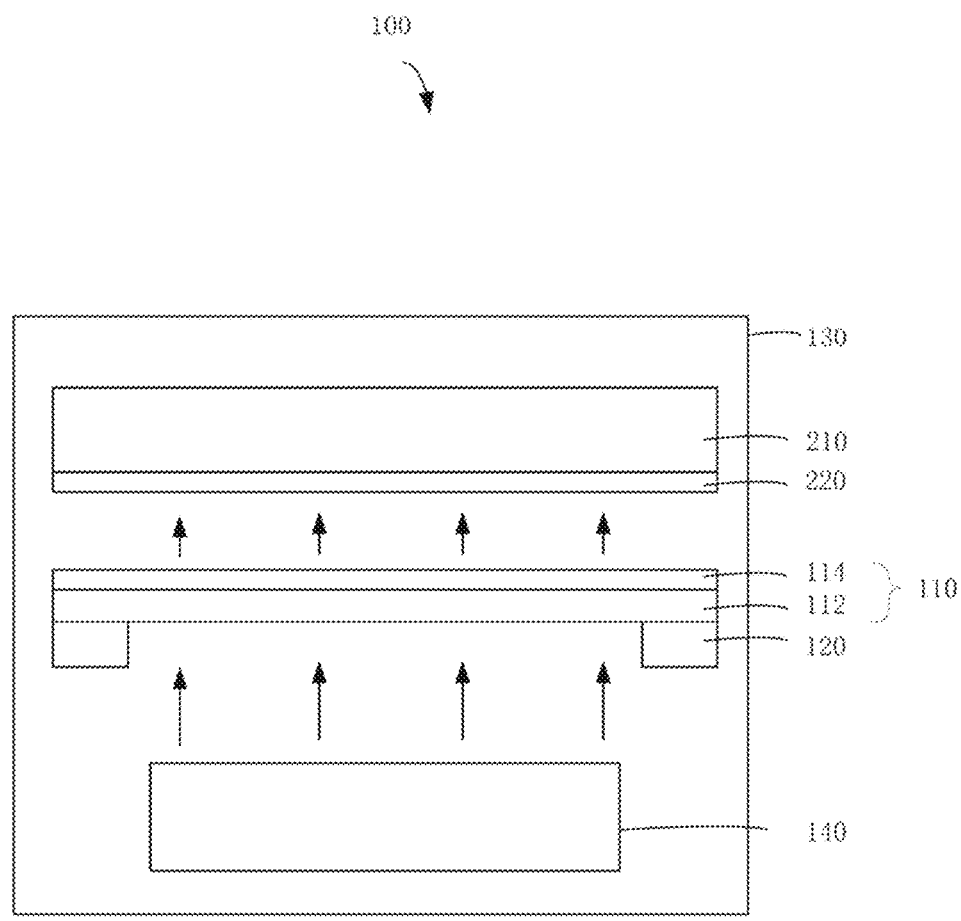
FIG. 5 is a schematic view of one embodiment of an apparatus for forming an organic thin film transistor.

Referring to FIG. 4 and FIG. 5, in one embodiment, a method for forming the top type and staggered organic thin film transistor 200 is provided. The organic thin film transistor 200 is formed in an apparatus 100. The organic semiconductor layer 230 is located on the surface of the interdigital electrode layer 220. The surface of the interdigital electrode layer 220 is a depositing surface. The method for forming the top type and staggered organic thin film transistor 200 comprises the following steps:

S1: forming the interdigital electrode layer 220 on the surface of the insulating substrate 210;

S2: forming the organic semiconductor layer 230 on a surface of the interdigital electrode layer 220, comprising:

S21: providing the evaporating source 110, wherein the evaporating source 110 comprises the carbon nanotube film structure 112 and the organic semiconductor material 114, and the organic semiconductor material 114 is located on a surface of the carbon nanotube film structure 112; and S22: spacing the evaporating source 110 from the interdigital electrode layer 220, and inputting an electromagnetic signal or an electrical signal to heat the carbon nanotube film structure 112 to gasify the organic semiconductor material 114 and form the organic semiconductor layer 230 on the surface of the interdigital electrode layer 220, wherein the interdigital electrode layer 220 is electrically connected to the organic semiconductor layer 230;

S3: forming the insulating layer 260 to cover the organic semiconductor layer 230; and S4: forming the gate electrode 250 on the insulating layer 260.

In the step S1, a method of forming the interdigital electrode layer 220 on the surface of the substrate 210 comprises the following steps:

S11: cleaning the substrate 210;

S12: depositing an interdigital electrode film on a surface of the substrate 210; S13: locating a mask on the interdigital electrode film and photoetching the interdigital electrode film to form an interdigital electrode layer; and S14, removing the mask to form the interdigital electrode layer.

In the step S12, the interdigital electrode film can be formed by conventional methods, such as vapor deposition, sputtering, coating or laying. In the S13, a pattern of the mask can be selected according to a required pattern of the interdigital electrode layer 220. In the S14, the mask is removed by wet etching to obtain the interdigital electrode layer 220.

In the step S21, the carbon nanotube film structure 112 is a carrying structure for the organic semiconductor material 114. The organic semiconductor material 114 is located on a surface of the carbon nanotube film structure 112. The carbon nanotube film structure 112 is configured to form a free-standing structure and can be suspended by supports. The organic semiconductor material 114 is located on a suspended surface of carbon nanotube film structure 112. In one embodiment, two supports 120 are provided. The two supports 120 are spaced from each other and disposed on opposite two ends of the carbon nanotube film structure 112. The carbon nanotube film structure 112 is suspended by the two supports 120.

The carbon nanotube film structure 112 comprises a single carbon nanotube film, or at least two stacked carbon nanotube films. The carbon nanotube film comprises a plurality of nanotubes. The plurality of nanotubes are generally parallel to each other, and arranged substantially parallel to a surface of the carbon nanotube film structure 112. The carbon nanotube film structure 112 has uniform thickness. The carbon nanotube film can be regarded as a macro membrane structure. In the macro membrane structure, an end of one carbon nanotube is joined to another end of an adjacent carbon nanotube arranged substantially along the same direction by Van der Waals attractive force. The carbon nanotube film structure 112 and the carbon nanotube film have a macro area and a microscopic area. The macro area denotes a membrane area of the carbon nanotube film structure 112 or the carbon nanotube film when the carbon nanotube film structure 112 or the carbon nanotube film is regarded as a membrane structure. In terms of a microscopic area, the carbon nanotube film structure 112 or the carbon nanotube film is a network structure having a large number of nanotubes joined end to end. The microscopic area signifies a surface area of the carbon nanotubes actually carrying the organic semiconductor material 114.

In one embodiment, the carbon nanotube film is formed by drawing from a carbon nanotube array. This carbon nanotube array is grown on a growth surface of a substrate by chemical vapor deposition method. The carbon nanotubes in the carbon nanotube array are substantially parallel to each other and perpendicular to the growth surface of the substrate. Adjacent carbon nanotubes make mutual contact and combine by van der Waals forces. By controlling the growth conditions, the carbon nanotube array is substantially free of impurities such as amorphous carbon or residual catalyst metal particles. The carbon nanotube array being substantially free of impurities with carbon nanotubes in close contact with each other, there is a larger van der Waals forces between adjacent carbon nanotubes. When carbon nanotube fragments (CNT fragments) are drawn, adjacent carbon nanotubes are continuously drawn out end to end by van der Waals forces to form a free-standing and uninterrupted macroscopic carbon nanotube film. The carbon nanotube array made of carbon nanotubes drawn end to end is also known as a super-aligned carbon nanotube array. In order to grow the super-aligned carbon nanotube array, the growth substrate material can be a P-type silicon, an N-type silicon, or a silicon oxide substrate.

Figure 6:
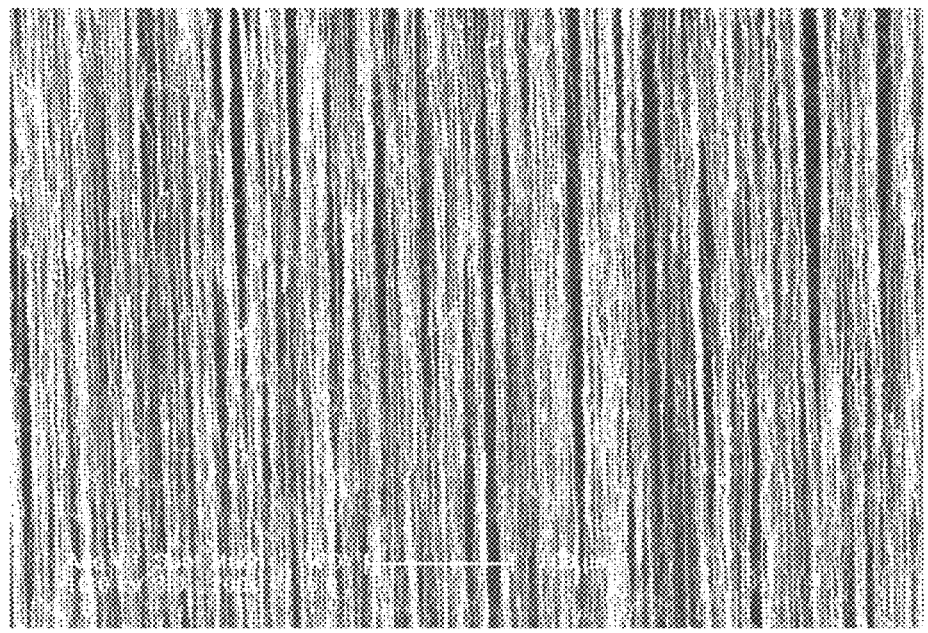
FIG. 6 is a scanning electron microscope (SEM) image of a carbon nanotube film drawn from a carbon nanotube array.

The carbon nanotube film includes a plurality of carbon nanotubes that can be joined end to end and arranged substantially along the same direction. Referring to FIG. 6, a majority of carbon nanotubes in the carbon nanotube film can be oriented along a preferred orientation, meaning that a large number of the carbon nanotubes in the carbon nanotube film are arranged substantially along the same direction. An end of one carbon nanotube is joined to another end of an adjacent carbon nanotube arranged substantially along the same direction by Van der Waals attractive force. A small number of the carbon nanotubes are randomly arranged in the carbon nanotube film, and has a small if not negligible effect on the larger number of the carbon nanotubes in the carbon nanotube film arranged substantially along the same direction.

More specifically, the carbon nanotube drawn film includes a plurality of successively oriented carbon nanotube segments joined end-to-end by Van der Waals attractive force therebetween. Each carbon nanotube segment includes a plurality of carbon nanotubes substantially parallel to each other and joined by Van der Waals attractive force therebetween. The carbon nanotube segments can vary in width, thickness, uniformity, and shape. The carbon nanotubes in the carbon nanotube drawn film are also substantially oriented along a preferred orientation.

Microscopically, the carbon nanotubes oriented substantially along the same direction may not be perfectly aligned in a straight line, and some curve portions may exist. It can be understood that some carbon nanotubes located substantially side by side and oriented along the same direction in contact with each other cannot be excluded. The carbon nanotube film includes a plurality of gaps between the adjacent carbon nanotubes so that the carbon nanotube film can have better transparency and higher specific surface area.

The carbon nanotube film is capable of forming a free-standing structure. The term "free-standing structure" can be defined as a structure that does not require a substrate for support. For example, a free standing structure can sustain the weight of itself when it is hoisted by a portion thereof without any damage to its structural integrity. So, if the carbon nanotube drawn film is placed between two separate supports, a portion of the carbon nanotube drawn film, not in contact with the two supports, would be suspended between the two supports and yet maintain film structural integrity. The free-standing structure of the carbon nanotube drawn film is realized by the successive carbon nanotubes joined end to end by Van der Waals attractive force.

The carbon nanotube film has a small and uniform thickness in a range from about 0.5 nm to 10 microns. Since the carbon nanotube film drawn from the carbon nanotube array can form the free-standing structure only by van der Waals forces between the carbon nanotubes, the carbon nanotube film has a large specific surface area. In one embodiment, the specific surface area of the carbon nanotube film measured by the BET method is in a range from about 200 $m^2/g$ to 2600 $m^2/g$. A mass per unit area of the carbon nanotube film is in a range from about 0.01 $g/m^2$ to about 0.1 $g/m^2$ (area here refers to the macro area of the carbon nanotube film). In another embodiment, the mass per unit area of the carbon nanotube film is about 0.05 $g/m^2$. Since the carbon nanotube film has a minimal thickness and the heat capacity of the carbon nanotube is itself small, the carbon nanotube film has small heat capacity per unit area. In one embodiment, the heat capacity per unit area of the carbon nanotube film is less than $2 \times 10^{-4}$ J/cm$^2$·K.

Figure 7:
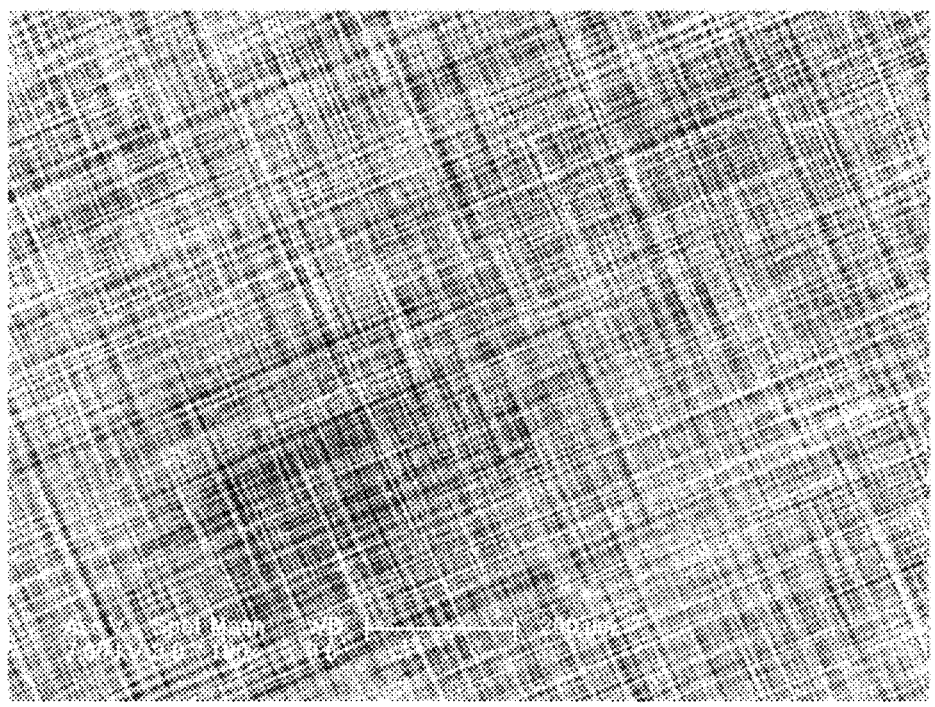
FIG. 7 is a SEM image of a carbon nanotube film structure.

The carbon nanotube film structure 112 may includes at least two stacked carbon nanotube films. In one embodiment, a number of layers of the stacked carbon nanotube film is 50 layers or less. In another embodiment, the number of layers of the stacked carbon nanotube film is 10 layers or less. Additionally, an angle can exist between the orientation of carbon nanotubes in adjacent carbon nanotube films. Adjacent carbon nanotube films can be combined by only Van der Waals attractive forces therebetween without the need of an adhesive. An angle between the aligned directions of the carbon nanotubes in two adjacent carbon nanotube films can range from about 0 degrees to about 90 degrees. In one embodiment, referring to FIG. 7, the carbon nanotube film structure 112 includes at least two stacked carbon nanotube films, and the angle between the aligned directions of the carbon nanotubes in the two adjacent carbon nanotube films is 90 degrees.

The organic semiconductor material 114 is disposed on the surface of the carbon nanotube film structure 112 by a plurality of methods, such as solution method, vapor deposition method, plating method or chemical plating method. The deposition method may be chemical vapor deposition (CVD) method or physical vapor deposition (PVD) method.

A solution method for disposing the organic semiconductor material 114 on the surface of the carbon nanotube film structure 112 comprises the steps of: (211) dissolving or uniformly dispersing the organic semiconductor material 114 in a solvent to form a mixture; (212) uniformly attaching the mixture to the carbon nanotube film structure 112 by spray coating method, spin coating method, or dip coating method; (213) evaporating and drying the solvent to make the organic semiconductor material 114 uniformly attach on the surface of the carbon nanotube film structure 112. In the step (211), the mixture can be a solution or a dispersion.

When the organic semiconductor material 114 includes a plurality kinds of material, the plurality of materials can be dissolved in a liquid phase solvent and mixed with a required ratio in advance so that the plurality of materials can be disposed on different locations of the carbon nanotube film structure 112 by the required ratio.

The step (212) and the step (213) may be repeated a plurality of times so that the organic semiconductor material 114 can have a required amount on the surface of the carbon nanotube film structure 112.

Figure 8:
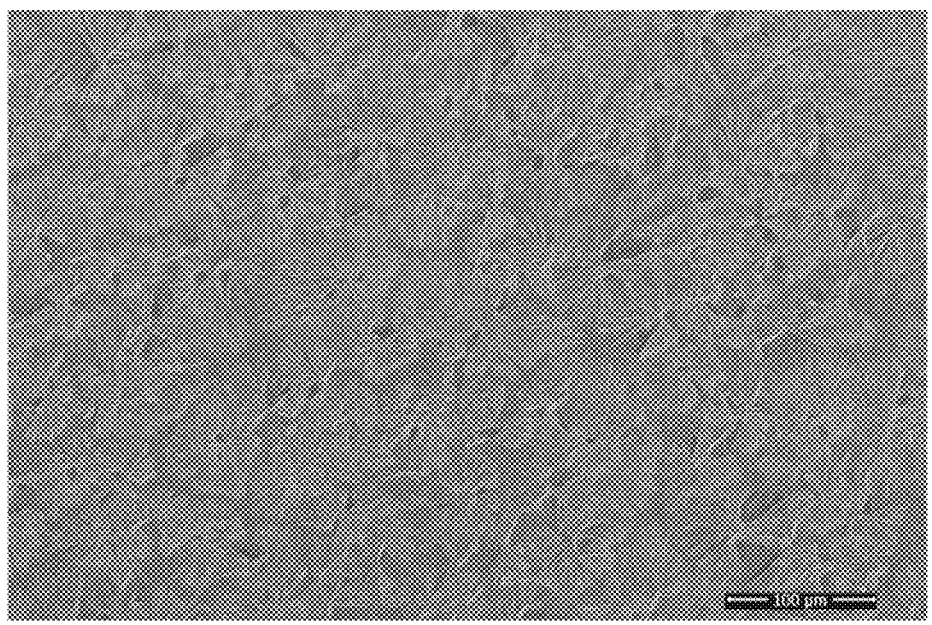
FIG. 8 and FIG. 9 are SEM images of one embodiment of the evaporating source under different resolutions.
Figure 9:
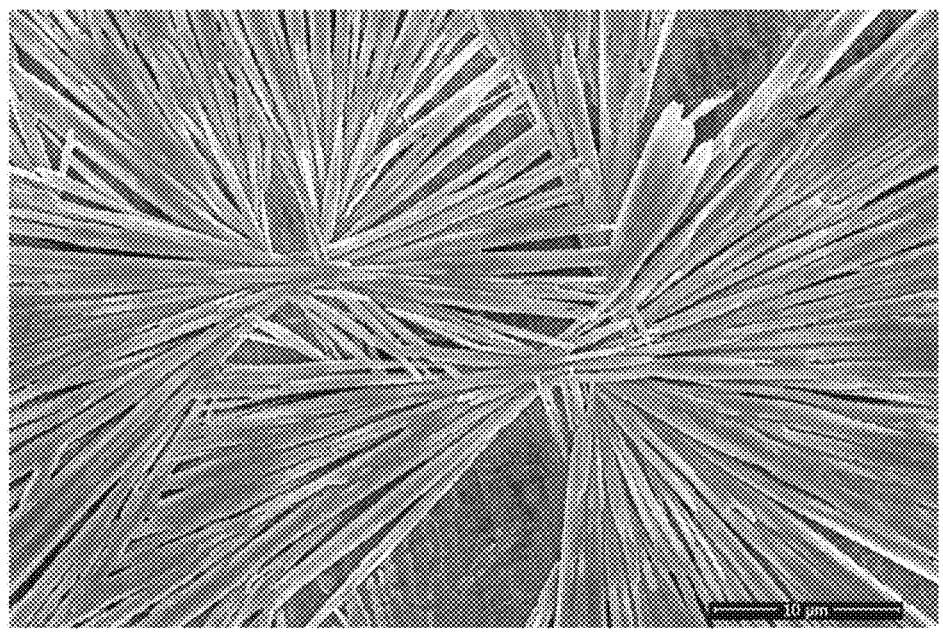

Referring FIG. 8 and FIG. 9, in one embodiment, in the S21, a solution method for depositing the photoactive material 114 on the surface of the carbon nanotube film structure 112 comprises steps of: (a) dispersing methyl ammonium iodide and lead iodide uniformly in an organic solvent with a stoichiometric ratio to form a dispersion; (b) spraying the dispersion on the surface of the carbon nanotube film structure 112; (c) evaporating and drying the organic solvent on the surface of the carbon nanotube film structure 112. The step of spraying and drying can be repeated many times so that the photoactive material 114 on the surface of the carbon nanotube film structure 112 has a required amount.

The organic semiconductor material 114 is adhered on and coats the surface of the carbon nanotube film structure 112. Macroscopically, the organic semiconductor material 114 can be seen as a layer formed on at least one surface of the carbon nanotube film structure 112. In one embodiment, the organic semiconductor material 114 is coated on two surfaces of the carbon nanotube film structure 112. The organic semiconductor material 114 and the carbon nanotube film structure 112 form a composite membrane. In one embodiment, a thickness of the composite membrane is 100 microns or less. In another embodiment, the thickness of the composite membrane is 5 microns or less. An amount of the organic semiconductor material 114 carried per unit area of the carbon nanotube film structure 112 is small. Thus, in microscopic terms, a morphology of the organic semiconductor material 114 may be nanoscale particles or layers with nanoscale thickness, being attached to a single carbon nanotube surface or the surfaces of a few carbon nanotubes. In one embodiment, the morphology of the organic semiconductor material 114 is particles. A diameter of the particles is in a range from about 1 nanometer to 500 nanometers. In another embodiment, the morphology of the organic semiconductor material 114 is a layer. A thickness of the organic semiconductor material 114 is in a range from about 1 nanometer to 500 nanometers. The organic semiconductor material 114 can completely cover and coat a single carbon nanotube for all or part of its length. The morphology of the organic semiconductor material 114 coated on the surface of the carbon nanotube film structure 112 is associated with the amount of the organic semiconductor material 114, species of the organic semiconductor material 114, a wetting performance of the carbon nanotubes, and other properties. For example, the organic semiconductor material 114 is more likely to be particle when the organic semiconductor material 114 is not soaked in the surface of the carbon nanotube. The organic semiconductor material 114 is more likely to uniformly coat a single carbon nanotube surface to form a continuous layer when the organic semiconductor material 114 is soaked in the surface of carbon nanotubes. In addition, when the organic semiconductor material 114 is an organic material having high viscosity, it may form a continuous film on the surface of the carbon nanotube film structure 112. No matter what the morphology of the organic semiconductor material 114 may be, the amount of the organic semiconductor material 114 carried by per unit area of the carbon nanotube film structure 112 is small. Thus, the electromagnetic signal or the electrical signal can instantaneously and completely gasify the organic semiconductor material 114. In one embodiment, the organic semiconductor material 114 is completely gasified within 1 second. In another embodiment, the organic semiconductor material 114 is completely gasified within 10 microseconds. The organic semiconductor material 114 is uniformly disposed on the surface of the carbon nanotube film structure 112, so that different locations of the carbon nanotube film structure 112 carry substantially equal amounts of the organic semiconductor material 114.

In the step S22, the evaporating source 110 is spaced from the interdigital electrode layer 220. A distance between the interdigital electrode layer 220 and the carbon nanotube film structure 112 is substantially equal. The carbon nanotube film structure 112 is substantially parallel to the depositing surface of the interdigital electrode layer 220. In one embodiment, the carbon nanotube film structure 112 coated with the organic semiconductor material 114 is spaced from and faces to the depositing surface of the interdigital electrode layer 220, and a distance between the carbon nanotube film structure 112 and the depositing surface of the interdigital electrode layer 220 is in a range from about 1 micrometer to about 10 millimeters. The area of the depositing surface of the interdigital electrode layer 220 is equal or less than the macro area of the carbon nanotube film structure 112. Thus, a gaseous organic semiconductor material can reach the depositing surface of the interdigital electrode layer 220 substantially at the same time.

The step S22 can be carried out in atmosphere or in vacuum. In one embodiment, the evaporating source 110 is located in a vacuum chamber 130. The electromagnetic signal or the electrical signal is inputted to the carbon nanotube film structure 112 to evaporate the organic semiconductor material 114 and form the organic semiconductor layer 230 on the depositing surface of the interdigital electrode layer 220.

When the electromagnetic signal or the electrical signal is inputted to heat the carbon nanotube film structure 112, the organic semiconductor material 114 is rapidly heated to a evaporation or sublimation temperature. Since per unit area of the carbon nanotube film structure 112 carries a small amount of the organic semiconductor material 114, all the organic semiconductor material 114 may instantly gasify. The carbon nanotube film structure 112 and the depositing surface of the interdigital electrode layer 220 are parallel to and spaced from each other. In one embodiment, the distance between the depositing surface of the interdigital electrode layer 220 and the carbon nanotube film structure 112 is in a range from about 1 micrometer to about 10 millimeters. Since the distance between the carbon nanotube film structure 112 and the depositing surface of the interdigital electrode layer 220 is small, the gaseous organic semiconductor material evaporated from the carbon nanotube film structure 112 is rapidly attached to the depositing surface of the interdigital electrode layer 220 to form the organic semiconductor layer 230. The area of the depositing surface is equal or less than the macro area of the carbon nanotube film structure 112. The carbon nanotube film structure 112 can completely cover the depositing surface of the interdigital electrode layer 220. Thus, the organic semiconductor material 114 is evaporated to the depositing surface of the interdigital electrode layer 220 as a correspondence to the carbon nanotube film structure 112 to form the organic semiconductor layer 230. Since the organic semiconductor material 114 is uniformly carried by the carbon nanotube film structure 112, the organic semiconductor layer 230 is also a uniform structure. When the organic semiconductor material 114 comprises the plurality of materials, a proportion of the plurality of materials is same in different locations of the carbon nanotube film structure 112. Thus, the plurality of materials still has same proportion in the gaseous organic semiconductor material, and a uniform organic semiconductor layer 230 can be formed on the depositing surface of the interdigital electrode layer 220.

The electromagnetic signal can be inputted to the carbon nanotube film structure 112 by an electromagnetic signal input device 140. The electromagnetic signal input device 140 may be located in the vacuum chamber 130 or outside the vacuum chamber 130 as long as an emitted electromagnetic signal can be transmitted to the carbon nanotube film structure 112. An average power density of the electromagnetic signal is in a range from about 100 mW/mm$^2$ to 20 W/mm$^2$. Since the structure of the carbon nanotube film structure 112 has a large specific surface area, the carbon nanotube film structure 112 can quickly exchange heat with surrounding medium, and heat signals generated by the carbon nanotube film structure 112 can quickly heat the organic semiconductor material 114. Since the amount of the organic semiconductor material 114 disposed on per unit macro area of the carbon nanotube film structure 112 is small, the organic semiconductor material 114 can be completely gasified instantly by the heat signals.

Figure 10:
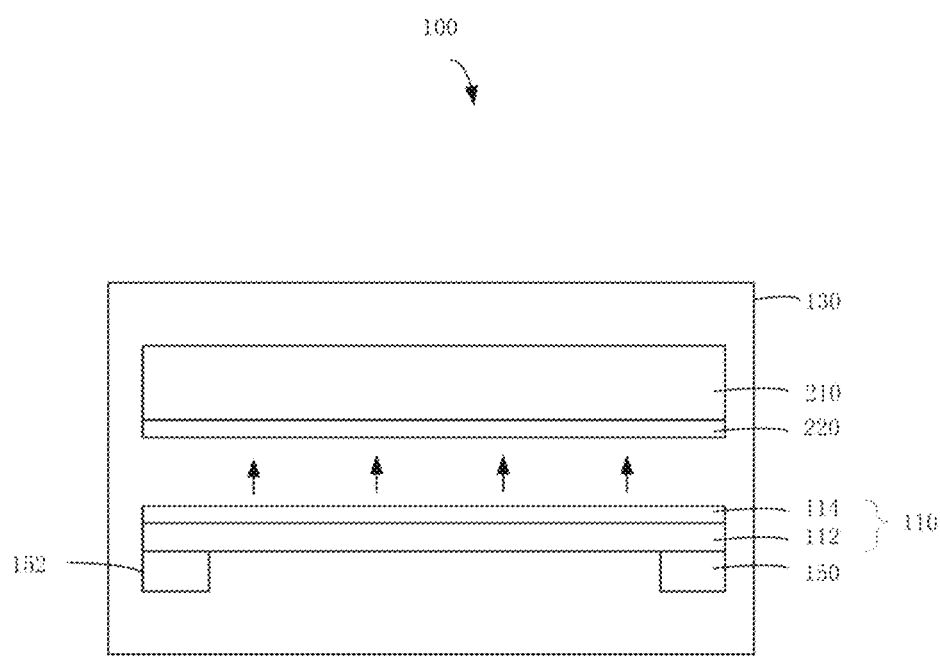
FIG. 10 is a schematic view of another embodiment of the apparatus for forming the organic thin film transistor.

Referring FIG. 10, the electrical signal can be inputted to the carbon nanotube film structure 112 by a first electrical signal input electrode 150 and a second electrical signal input electrode 152. The first electrical signal input electrode 150 and the second electrical signal input electrode 152 are spaced from each other and electrically connected to the carbon nanotube film structure 112. In one embodiment, the carbon nanotube film structure 112 is suspended by the first electrical signal input electrode 150 and the second electrical signal input electrode 152. The carbon nanotube film structure 112 is a resistive element. The carbon nanotube film structure 112 has the small heat capacity per unit area, and has the large specific surface area but a minimal thickness. In one embodiment, the heat capacity per unit area of the carbon nanotube film structure 112 is less than $2 \times 10^{-4}$ J/cm$^2$·K. In another embodiment, the heat capacity per unit area of the carbon nanotube film structure 112 is less than $1.7 \times 10^{-6}$ J/cm$^2$·K. The specific surface area of the carbon nanotube film structure 112 is larger than 200 m$^2$/g. The thickness of the carbon nanotube film structure 112 is less than 100 micrometers. The first electrical signal input electrode 150 and the second electrical signal input electrode 152 input the electrical signal to the carbon nanotube film structure 112. Since the carbon nanotube film structure 112 has the small heat capacity per unit area, the carbon nanotube film structure 112 can convert electrical energy to heat quickly, and a temperature of the carbon nanotube film structure 112 can rise rapidly. Since the carbon nanotube film structure 112 has the large specific surface area and is very thin, the carbon nanotube film structure 112 can rapidly transfer heat to the organic semiconductor material 114. The organic semiconductor material 114 is rapidly heated to the evaporation or sublimation temperature.

The first electrical signal input electrode 150 and the second electrical signal input electrode 152 are electrically connected to the carbon nanotube film structure 112. In one embodiment, the first electrical signal input electrode 150 and the second electrical signal input electrode 152 are directly disposed on the surface of the carbon nanotube film structure 112. The first electrical signal input electrode 150 and the second electrical signal input electrode 152 can input a current to the carbon nanotube film structure 112. The first electrical signal input electrode 150 and the second electrical signal input electrode 152 are spaced from each other and disposed at either end of the carbon nanotube film structure 112.

In one embodiment, the plurality of carbon nanotubes in the carbon nanotube film structure 112 extends from the first electrical signal input electrode 150 to the second electrical signal input electrode 152. When the carbon nanotube film structure 112 consists of one carbon nanotube film, or of at least two films stacked along a same direction (i.e., the carbon nanotubes in different carbon nanotube films being arranged in a same direction and parallel to each other), the plurality of carbon nanotubes of the carbon nanotube film structure 112 extend from the first electrical signal input electrode 150 to the second electrical signal input electrode 152. In one embodiment, the first electrical signal input electrode 150 and the second electrical signal input electrode 152 are linear structures and are perpendicular to extended directions of the carbon nanotubes of at least one carbon nanotube film in the carbon nanotube film structure 112. In one embodiment, the first electrical signal input electrode 150 and the second electrical signal input electrode 152 are same as a length of the carbon nanotube film structure 112, the first electrical signal input electrode 150 and the second electrical signal input electrode 152 thus extending from one end of the carbon nanotube film structure 112 to the other end. Thus, each of the first electrical signal input electrode 150 and the second electrical signal input electrode 152 is connected to two ends of the carbon nanotube film structure 112.

The carbon nanotube film structure 112 is the freestanding structure and can be suspended by the first electrical signal input electrode 150 and the second electrical signal input electrode 152. In one embodiment, the first electrical signal input electrode 150 and the second electrical signal input electrode 152 have sufficient strength to support the carbon nanotube film structure 112, and two supports 120 may be omitted. The first electrical signal input electrode 150 and the second electrical signal input electrode 152 may be conductive wires or conductive rods.

In the step S22, the electrical signal is inputted to the carbon nanotube film structure 112 through the first electrical signal input electrode 150 and the second electrical signal input electrode 152. When the electric signal is a direct current signal, the first electrical signal input electrode 150 and the second electrical signal input electrode 152 are respectively electrically connected to a positive and a negative of a direct current source. The direct current power inputs a direct current signal to the carbon nanotube film structure 112 through the first electrical signal input electrode 150 and the second electrical signal input electrode 152. When the electrical signal is an alternating current signal, the first electrical signal input electrode 150 is electrically connected to an alternating current source, and the second electrical signal input electrode 152 is connected to earth. The temperature of the carbon nanotube film structure 112 can reach the gasification temperature of the organic semiconductor material 114 by inputting an electrical signal power to the evaporating source 110. The electrical signal power can be calculated according to the formula $\sigma T^4 S$. Wherein $\sigma$ represents Stefan-Boltzmann constant; T represents the gasification temperature of the organic semiconductor material 114; and S represents the macro area of the carbon nanotube film structure 112. The larger the macro area of the carbon nanotube film structure 112 and the higher the gasification temperature of the organic semiconductor material 114, the greater the electrical signal power. Since the carbon nanotube film structure 112 has the small heat capacity per unit area, the carbon nanotube film structure 112 can quickly generate thermal response to raise the temperature. Since the carbon nanotube film structure 112 has the large specific surface area, the carbon nanotube film structure 112 can quickly exchange heat with surrounding medium, and heat signals generated by the carbon nanotube film structure 112 can quickly heat the organic semiconductor material 114. Since the amount of the organic semiconductor material 114 disposed on per unit macro area of the carbon nanotube film structure 112 is small, the organic semiconductor material 114 can be completely gasified instantly by the heat signals.

Figure 11:
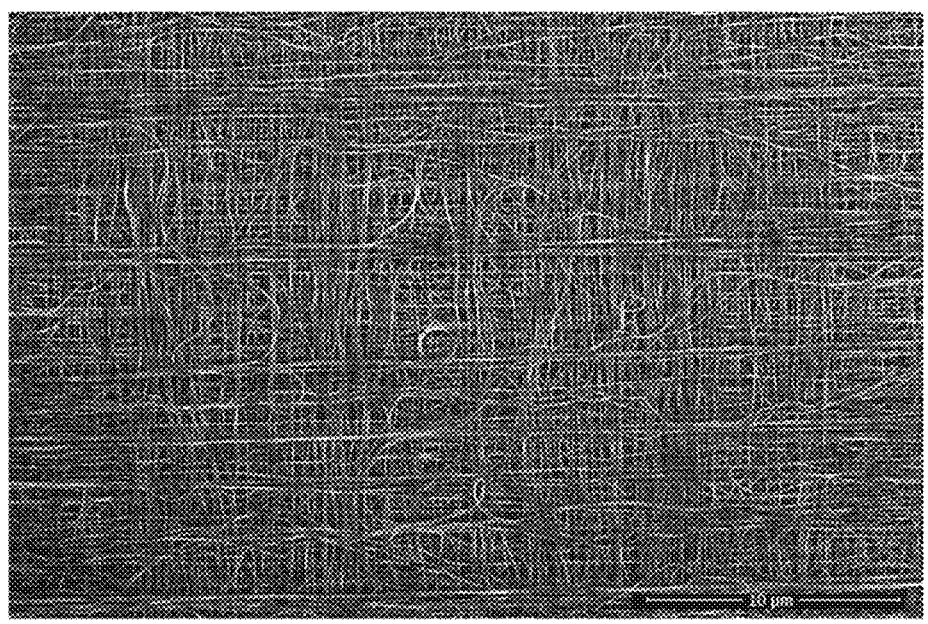
FIG. 11 is a SEM of one embodiment of the evaporating source after evaporation.
Figure 12:
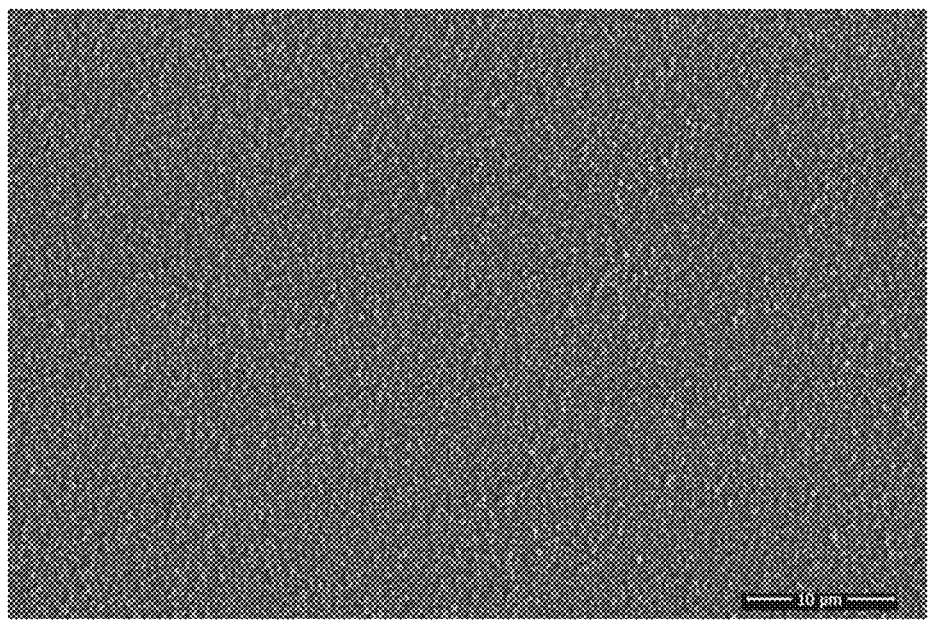
FIG. 12 is a SEM image of one embodiment of an organic semiconductor layer.
Figure 13:
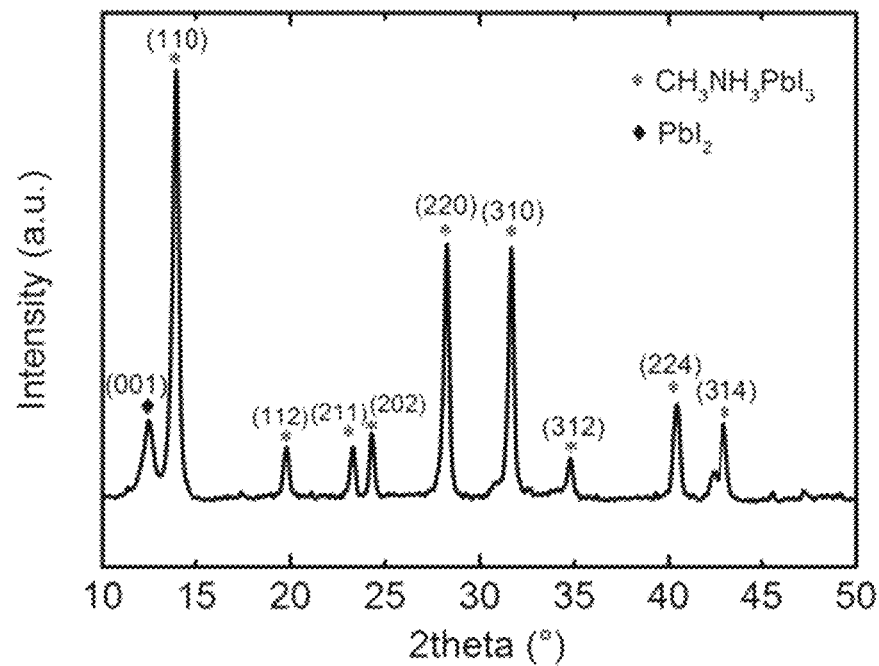
FIG. 13 is an X-ray diffraction (XRD) image of one embodiment of the organic semiconductor layer.

Referring FIG. 11 and FIG. 12, in one embodiment, after inputting the electrical current to the carbon nanotube film structure 112, the temperature of the carbon nanotube film structure 112 rises quickly, the mixture of the methylammonium iodide and the lead iodide located on the surface of the carbon nanotube film structure 112 is instantly gasified, and a perovskite structure $CH_3NH_3PbI_3$ film is formed on the depositing surface of the interdigital electrode layer 220. FIG. 11 shows a structure of the evaporating source 110 after vacuum evaporation. After evaporating the photoactive material 114 located on the surface structure of the carbon nanotube film structure 112, the carbon nanotube film structure 112 retains an original network structure, and the carbon nanotubes of the carbon nanotube film structure 112 are still joined end to end. FIG. 12 shows that the methylammonium iodide and the lead iodide continue a chemical reaction after gasification, and form a thin film having a uniform thickness on the depositing surface of the interdigital electrode layer 220. Referring to FIG. 13, the thin film can be tested by XRD (X-ray diffraction). The XRD can determine and show as patterns that a material of the thin film is the perovskite structure $CH_3NH_3PbI_3$.

In one embodiment, a method for forming the top type and coplanar organic thin film transistor 200 is provided. The depositing surface in this method is a surface of the insulating substrate 210. The method for forming the top type and coplanar organic thin film transistor 200 comprises the following steps:

T1: forming the organic semiconductor layer 230 on a surface of the insulating substrate 210, comprising:

T11: providing the evaporating source 110, wherein the evaporating source 110 comprises the carbon nanotube film structure 112 and the organic semiconductor layer material 114, and the organic semiconductor layer material 114 is located on the surface of the carbon nanotube film structure 112; and T12: spacing the evaporating source 110 from the insulating substrate 210, and inputting the electromagnetic signal or the electrical signal to heat the carbon nanotube film structure 112 to gasify the organic semiconductor material 114 and form the organic semiconductor layer 230 on the surface of the insulating substrate 210;

T2: forming the interdigital electrode layer 220 on a surface of the organic semiconductor layer 230, wherein the interdigital electrode layer 220 is electrically connected to the organic semiconductor layer 230;

T3: forming the insulating layer 260 to cover the organic semiconductor layer 230; and T4: forming the gate electrode 250 on a surface of the insulating layer 260.

In one embodiment, a method for forming the reverse coplanar organic thin film transistor 200 is provided. The depositing surface is the surface of the interdigital electrode layer 220. The method for forming the reverse coplanar organic thin film transistor 200 comprises the following steps:

M1: forming the gate electrode 250 on the surface the insulating substrate 210;

M2: forming the insulating layer 260 to cover the gate electrode 250;

M3: forming the interdigital electrode layer 220 on the insulating layer 260; and M4: forming the organic semiconductor layer 230 on the insulating layer 260 to cover and electrically connected to the interdigital electrode layer 220, comprising:

M41: providing the evaporating source 110, wherein the evaporating source 110 comprises the carbon nanotube film structure 112 and the organic semiconductor material 114, and the organic semiconductor material 114 is located on the surface of the carbon nanotube film structure 112; and M42: spacing the evaporating source 110 from the interdigital electrode layer 220, the source electrode 220, and the drain electrode 240, and inputting the electromagnetic signal or the electrical signal to heat the carbon nanotube film structure 112 to gasify the organic semiconductor material 114 and form the organic semiconductor layer 230 on the surface of the interdigital electrode layer 220.

In another embodiment, a method for forming the reverse staggered organic thin film transistor 200 is provided. The depositing surface is the surface of the insulating layer 260.

The method for forming the reverse staggered organic thin film transistor 200 comprises the following steps:

N1: forming the gate electrode 250 on the surface the insulating substrate 210;

N2: forming the insulating layer 260 to cover the gate electrode 250;

N3: forming the organic semiconductor layer 230 on the insulating layer 260, comprising:

N31: providing the evaporating source 110, wherein the evaporating source 110 comprises the carbon nanotube film structure 112 and the organic semiconductor material 114, and the organic semiconductor material 114 is located on the surface of the carbon nanotube film structure 112; and N32: spacing the evaporating source 110 from the insulating layer 260, and inputting the electromagnetic signal or the electrical signal to heat the carbon nanotube film structure 112 to gasify the organic semiconductor material 114 and form the organic semiconductor layer 230 on the surface of the insulating layer 260; and N4: forming the interdigital electrode layer 220 on the organic semiconductor layer 230, and the interdigital electrode layer 220 is electrically connected to the organic semiconductor layer 230.

Figure 14:
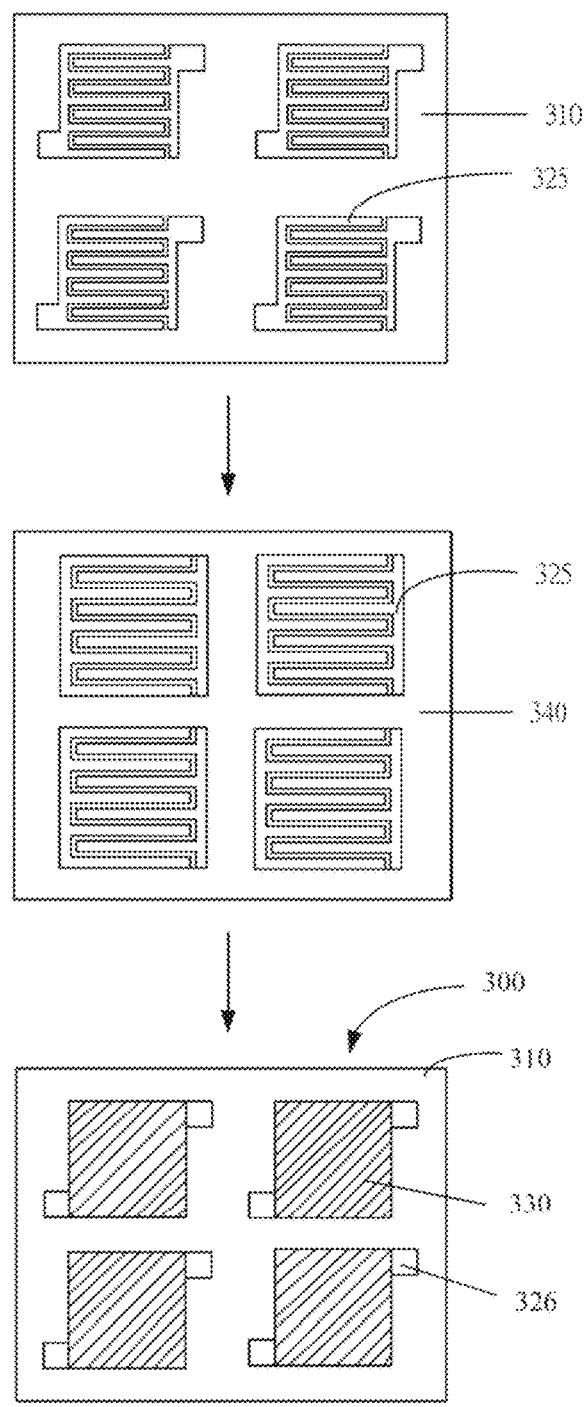
FIG. 14 is a flowchart of one embodiment of a method for forming the organic semiconductor layer.
Figure 15:
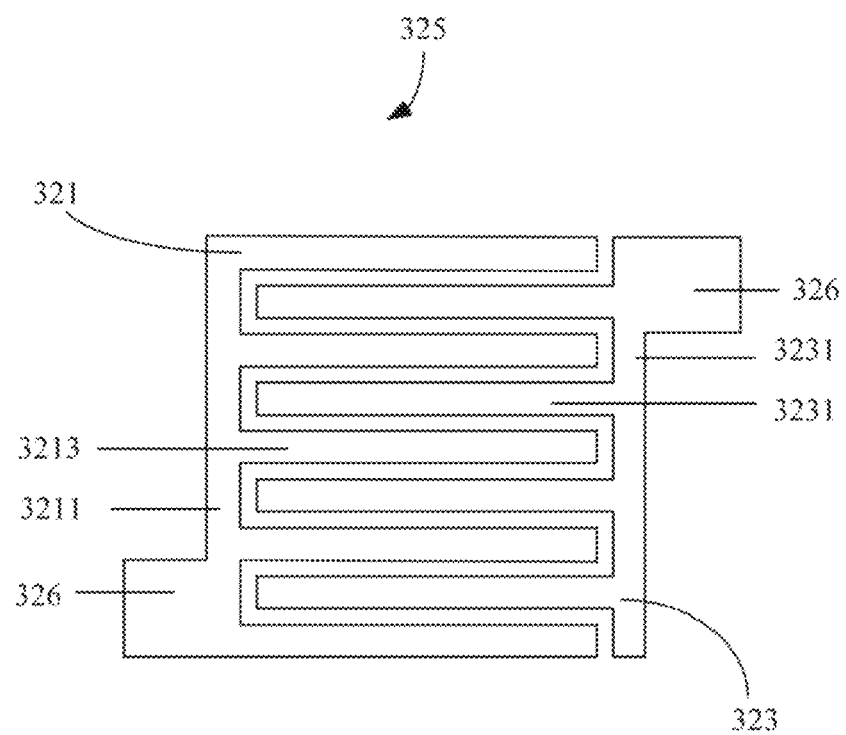
FIG. 15 is a schematic view of one embodiment of a sub-interdigital electrode layer.

Referring to FIG. 13 and FIG. 14, a method of forming an organic thin film transistor array 300 is provided. The method of forming the organic thin film transistor array 300 comprises the following steps:

S10: providing a substrate 310 and forming an interdigital electrode layer 320 on a surface of the substrate 310;

S20: disposing a patterned mask layer 340 on a surface of the substrate 310 to cover the substrate 310 and at least a portion of the interdigital electrode layer 320;

S30: obtaining an evaporating source 110, wherein the evaporating source 110 comprises a carbon nanotube film structure 112 and an organic semiconductor material 114, and the organic semiconductor material 114 is located on a surface of the carbon nanotube film structure 112;

S40: spacing the evaporating source 110 from the interdigital electrode layer 320, and inputting an electromagnetic signal or an electrical signal to heat the carbon nanotube film structure 112 to gasify the organic semiconductor material 114 and form an organic semiconductor layer 330 on a surface of the interdigital electrode layer 320;

S50: removing the patterned mask layer 340 to form a photodetector array 300;

S60: forming an insulating layer 360 to cover the organic semiconductor layer 330; and S70: forming a gate electrode 350 on the insulating layer 360.

The step S10 in the method of forming the organic thin film transistor array 300 is substantially the same as the S1 in the method of forming the organic thin film transistor 200, except that the pattern of the mask for forming the interdigital electrode layer 320 is different. In one embodiment, the interdigital electrode layer 320 comprises a plurality of sub-interdigital electrode layers 325. A structure of each of the sub-interdigital electrode layers 325 is substantially the same as the interdigital electrode layer 220.

Referring FIG. 14, each sub-interdigital electrode layer 325 comprises a first interdigital electrode 321 and a second interdigital electrode 323. The first interdigital electrode 321 comprises a first connection part 3213 and a plurality of first interdigital parts 3211. The plurality of first interdigital parts 3211 are in connection with the first connection part 3213. The plurality of first interdigital parts 3211 are parallel to and spaced from each other. The first connection part 3213 is used to electrically connect with an external power source.

The second interdigital electrode 323 comprises a second connection part 3233 and a plurality of second interdigital parts 3231. The plurality of second interdigital parts 3231 are in connection with the second connection part 3233. The plurality of second interdigital parts 2231 are parallel to and spaced from each other. The second connection part 3233 is used to electrically connect with an external power source. The plurality of first interdigital parts 3211 and the plurality of second interdigital parts 3231 are staggered and spaced from each other. A shape of a first interdigital electrode 321 and a second interdigital electrode 323 is not limited and can be selected according to actual needs. In one embodiment, a shape of the first connection part 3231 and the second connection part 3233 is "L". A shape of each first interdigital parts 3211 and second interdigital parts 3231 is rectangular strip.

In the step S20, the patterned mask layer 340 covers the substrate 310 and at least a portion of the interdigital electrode layer 320. In one embodiment, the patterned mask layer 340 covers the substrate 310, the first connection part 3231 and the second connection part 3233. A material of the patterned mask layer 340 can be metal, such as stainless steel, aluminum alloy. The patterned mask layer 340 has a plurality of through holes corresponding to the sub-interdigital electrode layer 325. The size of the through hole is smaller than the size of the sub-interdigital electrode layer 325 so that other portions of the sub-interdigital electrode layer 325 are exposed while the patterned mask layer 340 covering connection parts of the sub-interdigital electrode layer 325. The size of the through hole and the sub-interdigital electrode layer 325 can be selected according to the size of the organic semiconductor layer 330. In one embodiment, the shape of the first connection part 3231 and the second connection part 3233 is "L". The patterned mask layer 340 covers the substrate 310 and a protrusion 326 of the "L". The size of the through hole is a 500×500 μm² square. The material of the patterned mask layer 340 is stainless steel. In the S20, a patterned stainless steel layer is directly disposed on the surface of the substrate 310 to cover the substrate 310 and at least a portion of the interdigital electrode layer 320.

The step S30 in the method of forming the organic thin film transistor array 300 is the same as the step S21 in the method of forming the organic thin film transistor 200.

The step S40 in the method of forming the organic thin film transistor array 300 is substantially the same as the S22 in the method of forming the organic thin film transistor 200, except that the organic thin film transistor layer 330 is formed on an exposed interdigital electrode layer 320 not covered by the patterned mask layer 340.

In the step S50, after removing the patterned mask layer 340, a portion of the sub-interdigital electrode layer 325 not covered by the photoactive layer 330 is exposed to connect the power source. In one embodiment, after directly removing the patterned mask layer 340, the protrusion 326 of an "L" shaped structure of the first connection part 3213 and the second connection part 3233 is not covered by the photoactive layer 330 and are exposed to outside.

The step S60 in the method of forming the organic thin film transistor array 300 is the same as the step S3 in the method of forming the organic thin film transistor 200. The step S70 in the method of forming the organic thin film transistor array 300 is the same as the step S4 in the method of forming the organic thin film transistor 200.

The structure of the organic thin film transistor is simple because of using the interdigital electrode layer. The carbon nanotube film is free-standing structure and used to carry an organic semiconductor material. The carbon nanotube film has a large specific surface area and good uniformity so that the organic semiconductor material carried by the carbon nanotube film can uniformly distributed on the carbon nanotube film before evaporation. The carbon nanotube film can be heated instantaneously. Thus the organic semiconductor material can be completely gasified in a short time to form a uniform gaseous organic semiconductor material, and the uniform gaseous organic semiconductor material can be uniformly distributed over a large area. The distance between the depositing surface and the carbon nanotube film is small. Thus the organic semiconductor material carried on the carbon nanotube film can be substantially utilized to save the organic semiconductor material and improve the deposition rate.

Even though numerous characteristics and advantages of certain inventive embodiments have been set out in the foregoing description, together with details of the structures and functions of the embodiments, the disclosure is illustrative only. Changes may be made in detail, especially in matters of arrangement of parts, within the principles of the present disclosure to the full extent indicated by the broad general meaning of the terms in which the appended claims are expressed.

Depending on the embodiment, certain of the steps of methods described may be removed, others may be added, and the sequence of steps may be altered. It is also to be understood that the description and the claims drawn to a method may comprise some indication in reference to certain steps. However, the indication used is only to be viewed for identification purposes and not as a suggestion as to an order for the steps.

The embodiments shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure up to, and including the full extent established by the broad general meaning of the terms used in the claims. It will, therefore, be appreciated that the embodiments described above may be modified within the scope of the claims.

What is claimed is:

1. A method for making an organic thin film transistor, comprising:
    S1: applying an interdigital electrode layer on a surface of an insulating substrate;
    S2: forming an organic semiconductor layer on a surface of the interdigital electrode layer, wherein the forming the organic semiconductor layer comprises:
        S21: providing an evaporating source, wherein the evaporating source comprises a carbon nanotube film structure and an organic semiconductor material, and the organic semiconductor material is located on a carbon nanotube film structure surface; and
        S22: spacing the evaporating source from the interdigital electrode layer, and heating the carbon nanotube film structure to gasify the organic semiconductor material and form the organic semiconductor layer on an interdigital electrode layer surface;
    S3: locating an insulating layer to cover the organic semiconductor layer; and
    S4: forming a gate electrode on the insulating layer.

2. The method of claim 1, wherein the step of applying the interdigital electrode layer on the surface of the insulating substrate comprises:
    S11: cleaning the substrate;
    S12: depositing an interdigital electrode film on a surface of the substrate;
    S13: locating a mask on the interdigital electrode film and photoetching the interdigital electrode film to form an interdigital electrode layer; and
    S14, removing the mask to form the interdigital electrode layer.

3. The method of claim 1, wherein the organic semiconductor material is disposed on the carbon nanotube film structure surface by a solution method, a vapor deposition method, a plating method or a chemical plating method.

4. The method of claim 1, wherein the organic semiconductor material is disposed on the carbon nanotube film structure surface by a solution method, and the solution method comprises:
    S11, dispersing an organic semiconductor material in a solvent to form a mixture;
    S12, forming the mixture on the carbon nanotube film structure;
    S13, drying the solvent to make the organic semiconductor material uniformly formed on the carbon nanotube film structure surface.

5. The method of claim 1, wherein the organic semiconductor material comprises a plurality kinds of material, and the plurality of materials are dissolved in a liquid phase solvent and mixed with each other.

6. The method of claim 1, wherein in the S2, the evaporating source and the organic semiconductor material are located in a vacuum chamber.

7. The method of claim 1, wherein an electromagnetic signal is inputted to heat the carbon nanotube film structure by an electromagnetic signal input device.

8. The method of claim 1, wherein an electrical signal is inputted to heat the carbon nanotube film structure by a first electrical signal input electrode and a second electrical signal input electrode.

9. The method of claim 1, wherein a distance between the interdigital electrode layer surface and the carbon nanotube film structure is in a range from about 1 micrometer to about 10 millimeters.

10. The method of claim 1, wherein a heat capacity per unit area of the carbon nanotube film structure is less than $2 \times 10^{-4}$ J/cm$^2 \cdot$K, and a specific surface area of the carbon nanotube film structure is larger than 200 m$^2$/g.

11. The method of claim 1, wherein the carbon nanotube film structure comprises at least one carbon nanotube film, the least one carbon nanotube film comprises a plurality of nanotubes joined end to end by Van der Waals attractive force.

12. The method of claim 1, wherein the organic semiconductor material is $CH_3NH_3PbI_3$.

13. A method for forming an organic thin film transistor array comprising:
    S10: providing a substrate and forming an interdigitated electrode layer on a substrate surface;
    S20: disposing a patterned mask layer on the substrate surface to cover the substrate and at least a portion of the interdigitated electrode layer;
    S30: obtaining an evaporating source, wherein the evaporating source comprises a carbon nanotube film structure and an organic semiconductor material, and the organic semiconductor material is located on a carbon nanotube film structure surface;

S40: spacing the evaporating source from the interdigitated electrode layer, and heating the carbon nanotube film structure to gasify the organic semiconductor material and form an organic semiconductor layer on a interdigitated electrode layer surface;

S50: removing the patterned mask layer to form a photodetector array;

S60: forming an insulating layer to cover the organic semiconductor layer; and

S70: forming a gate electrode on the insulating layer.

14. The method of claim 13, wherein a distance between the interdigital electrode layer surface and the carbon nanotube film structure is in a range from about 1 micrometer to about 10 millimeters.

15. The method of claim 13, wherein a heat capacity per unit area of the carbon nanotube film structure is less than $2 \times 10^{-4}$ J/cm$^2$·K, and a specific surface area of the carbon nanotube film structure is larger than 200 m$^2$/g.

16. The method of claim 13, wherein the carbon nanotube film structure comprises at least one carbon nanotube film, the least one carbon nanotube film comprises a plurality of nanotubes joined end to end by Van der Waals attractive force.

17. The method of claim 13, wherein the organic semiconductor material is $CH_3NH_3PbI_3$.

* * * * *